US008672931B2

United States Patent
Goldboss et al.

(10) Patent No.: US 8,672,931 B2
(45) Date of Patent: Mar. 18, 2014

(54) CRYOSURGICAL DEVICE WITH METERED DOSE

(75) Inventors: Anthony Goldboss, Chicago, IL (US); Charles Incorvia, Northbrook, IL (US); Judy Goldboss, Chicago, IL (US)

(73) Assignee: 3JT Enterprises, LLC, Chicago, IL (US)

( * ) Notice: Subject to any disclaimer, the term of this patent is extended or adjusted under 35 U.S.C. 154(b) by 1306 days.

(21) Appl. No.: 12/193,317

(22) Filed: Aug. 18, 2008

(65) Prior Publication Data
US 2010/0042087 A1 Feb. 18, 2010

(51) Int. Cl.
*A61B 18/02* (2006.01)

(52) U.S. Cl.
USPC .................................. 606/22; 606/25; 606/26

(58) Field of Classification Search
USPC .................................. 606/20, 22, 23, 25, 26
See application file for complete search history.

(56) References Cited

U.S. PATENT DOCUMENTS

| | | | |
|---|---|---|---|
| 3,782,386 A | | 1/1974 | Barger et al. |
| 3,901,241 A | * | 8/1975 | Allen, Jr. ......................... 606/25 |
| 4,116,199 A | * | 9/1978 | Bryne ............................. 606/22 |
| 4,376,376 A | * | 3/1983 | Gregory .......................... 62/48.1 |
| 5,200,170 A | | 4/1993 | McDow |
| 5,290,273 A | | 3/1994 | Tan |
| 5,330,745 A | | 7/1994 | McDow |
| 5,516,505 A | | 5/1996 | McDow |
| 5,658,276 A | | 8/1997 | Griswold |
| 5,738,682 A | | 4/1998 | Jensma |
| 6,092,527 A | | 7/2000 | Jensma |
| 6,312,428 B1 | | 11/2001 | Eggers et al. |
| 6,387,090 B1 | * | 5/2002 | Jensma ........................... 606/23 |
| 2001/0035189 A1 | | 11/2001 | Dobak, III |
| 2006/0054634 A1 | | 3/2006 | Mekata |
| 2006/0116670 A1 | | 6/2006 | Scott et al. |
| 2006/0189968 A1 | | 8/2006 | Howlett et al. |
| 2006/0235375 A1 | | 10/2006 | Littrup et al. |
| 2007/0005048 A1 | * | 1/2007 | Niedbala et al. ................ 606/22 |
| 2008/0142555 A1 | * | 6/2008 | Marin et al. ................... 222/645 |
| 2008/0147055 A1 | | 6/2008 | Duong et al. |
| 2010/0288797 A1 | | 11/2010 | Sogaro |

FOREIGN PATENT DOCUMENTS

| | | |
|---|---|---|
| DE | 20 2007 013 747 | 9/2009 |
| GB | 1163573 | 9/1969 |
| WO | WO 2007/028975 A1 | 3/2007 |

OTHER PUBLICATIONS

International Preliminary Report on Patentability, dated Mar. 3, 2011, in corresponding International Application No. PCT/US2009/052832.
Written Opinion of the International Searching Authority, dated Oct. 6, 2009, in corresponding International Application No. PCT/US2009/052832.
Extended European Search Report, dated Nov. 18, 2011, in corresponding European approved Application No. 09 808 594.7.

\* cited by examiner

*Primary Examiner* — Michael Peffley
*Assistant Examiner* — Thomas Giuliani
(74) *Attorney, Agent, or Firm* — Cool Alex Ltd.

(57) ABSTRACT

A cryosurgical device and system is provided comprising a pressurized container, a metered valve that regulates the retrieval of a coolant solution stored in the pressurized container and regulates the volume of coolant solution dispensed with each actuation of the device, an actuator that engages the metered valve when engaged, and directs the coolant solution to an extension tube, which directs the coolant solution away from the pressurized container, and an applicator head configuring an open-ended enclosure attached to a distal end of the extension tube.

16 Claims, 4 Drawing Sheets

CRYOSURGICAL DEVICE WITH METERED DOSE

FIELD OF THE INVENTION

The present invention relates generally to the field of cryosurgical devices for cryosurgically treating skin diseases and more particularly to a cryosurgical device for applying a cryogenic refrigerant from a pressurized container in metered doses.

BACKGROUND OF THE INVENTION

Cryosurgery is the application of extreme cold to destroy abnormal or diseased tissue and can be used to treat a number of skin diseases and disorders. Cryosurgery is generally employed in the medical field for the removal of skin lesions from the body of a mammal, including the human body. When extreme cold is applied to abnormal cells, ice crystals can form inside the cells, which can rupture their cell membranes, thus destroying the cells. The extreme cold can also freeze blood vessels supplying blood to the abnormal cells.

Traditionally, liquid nitrogen has been used as the coolant solution in cryosurgery. However, other coolant solutions have been used and are known by those of skill in the art. Historically, the coolant solution was applied to the abnormal tissue with a cotton or foam swab.

More recently, however, methods were developed to spray the coolant solution onto the abnormal tissue. In these methods, the coolant solution is typically stored in a pressurized container, and, upon demand, an uncontrolled amount of coolant solution is dispensed from the container into a supply tube. In some methods, the coolant solution can exit the supply tube and be dispersed into a cone, cup, or speculum placed around the abnormal tissue to pool the solution. In other methods, the supply tube can have a porous tip applicator, for example a cotton or plastic foam applicator, located at the distal end of the tube. The coolant solution can accumulate in the applicator, and the applicator can be applied to the surface of the abnormal tissue.

When coolant solution is applied to a treatment area, the coolant solution must remain in contact with the treatment area for a period of time until what is called an ice ball, by those of ordinary skill in the art, is formed. The ice ball must be maintained for approximately 30 seconds and should be big enough to cover the treatment area, which includes the abnormal tissue as well as an area 1-2 mm around the abnormal tissue in all directions.

After the ice ball is formed, it is maintained for a sufficient period of time. During this time, the coolant solution vaporizes and evaporates. Part of the evaporation process is called bubbling by those of ordinary skill in the art, and it is desirable for a practitioner to be able to view bubbles during the bubbling process. As the bubbles begin to dissipate, a thawing process can begin. If a practitioner wishes to maintain the ice ball for a longer period of time, more coolant solution should be applied to the treatment area when the bubbles begin to dissipate.

Typically an ice ball will need to thaw for approximately one minute. Most destruction of the abnormal cells in the treatment area occurs during the thawing phase. The freeze and thaw cycle described above can be repeated as necessary depending on the size of the treatment area.

Devices used in connection with the above-described methods known by those of skill in the art incorporate several disadvantages. First, the coolant solution is often wasted. When an uncontrolled amount of coolant solution is dispensed from the container, a large portion of the coolant solution is wasted due to the uncontrolled dispensing from the container and what is called blowback by those of skill in the art. When this happens, an excessive amount of coolant solution is released into the surrounding atmosphere rather than directed onto the abnormal tissue.

When a cone is used by a practitioner in connection with applying coolant solution to a treatment area, both hands are often required for application. As such, often a second person is required to assist when treating difficult to reach areas.

When a porous tip applicator is used to apply the coolant solution to abnormal tissue, an excessive amount of coolant solution is often delivered through the supply tube to saturate the applicator. When this happens, coolant solution is dispensed directly into the atmosphere and thus, coolant solution is wasted. Furthermore, not all of the coolant solution absorbed in or on the applicator reaches the abnormal tissue. A portion of the coolant solution remains in or on the applicator when applied to the treatment area. Additionally, the shapes of these applicators do not allow the coolant solution to be distributed evenly or onto a precisely demarcated area.

Another disadvantage of devices used in connection with the above-described methods is that the coolant solution is dispersed in an uncontrolled manner. Thus, coolant solution is often sprayed or splashed outside of the intended treatment area onto the patient's body or a practitioner's hands or arm.

There is thus a continuing, ongoing need for a cryosurgical device for cryosurgically treating skin lesions that provides for effective treatment of the abnormal tissue, that does not waste the coolant solution used in connection with the device, and that evenly distributes a controlled amount of coolant solution to a well defined area.

SUMMARY OF THE INVENTION

Accordingly, it is a benefit of the present invention to provide a cryosurgical device and system for cryosurgically treating skin disease and a method of using such a device and system that provides for the effective treatment of abnormal tissue.

It is further benefit of the present invention to provide a cryosurgical device and system for cryosurgically treating skin disease and a method of using such a device and system that does not waste the coolant solution used in connection with the device.

It is another benefit of the present invention to provide a cryosurgical device and system for cryosurgically treating skin disease and a method of using such a device and system to evenly distribute a controlled amount of coolant solution to a precisely demarcated area and to prevent spraying or splashing of the coolant solution onto undesired areas of the patient or practitioner.

It is still another benefit of the present invention to provide a cryosurgical device and system for cryosurgically treating skin disease and a method of using such a device and system that incorporates a metered valve for delivering a coolant solution to the abnormal tissue.

It is another benefit of the present invention to provide a cryosurgical device and system for cryosurgically treating skin diseases and a method of using such a device and system that facilitates a practitioner applying coolant solution to a treatment area to generate an ice ball, maintaining the ice ball for a sufficient period of time, observing bubbling, and actuating the device additional times as necessary to apply more coolant solution to maintain the ice ball for the necessary time period before thawing begins.

It is still another benefit of the present invention to provide a cryosurgical device and system for cryosurgically treating skin diseases and a method of using such a device and system that facilitates multiple freeze and thaw cycles occurring.

It is yet another benefit of the present invention to provide a cryosurgical device and system for cryosurgically treating skin disease and a method of using such a device and system that controls the duration of freezing the abnormal tissue to which the coolant solution is applied.

It is a further benefit of the present invention to provide a cryosurgical device and system for cryosurgically treating skin disease and a method of using such a device that allows for single handed operation of the device and system by a practitioner.

Finally, it is a benefit of the present invention to provide a method of using a cryosurgical device and system for cryosurgically treating skin disease and a method of using such a device and system that allows a user to effectively view and assess a treatment area while a coolant solution is being administered to the area.

In accordance with the present invention, all of these benefits as well as others not herein specifically identified, are generally achieved by the present cryosurgical device with a metered dose.

BRIEF DESCRIPTION OF THE DRAWINGS

Various examples of benefits, features and attendant advantages of the present invention will become fully appreciated as the same becomes better understood when considered in conjunction with the accompanying drawings, wherein:

FIG. 4d illustrates a fourth cross-sectional view of an applicator head in accordance with the first embodiment of the present invention;

DETAILED DESCRIPTION OF THE INVENTION

Figure 1:
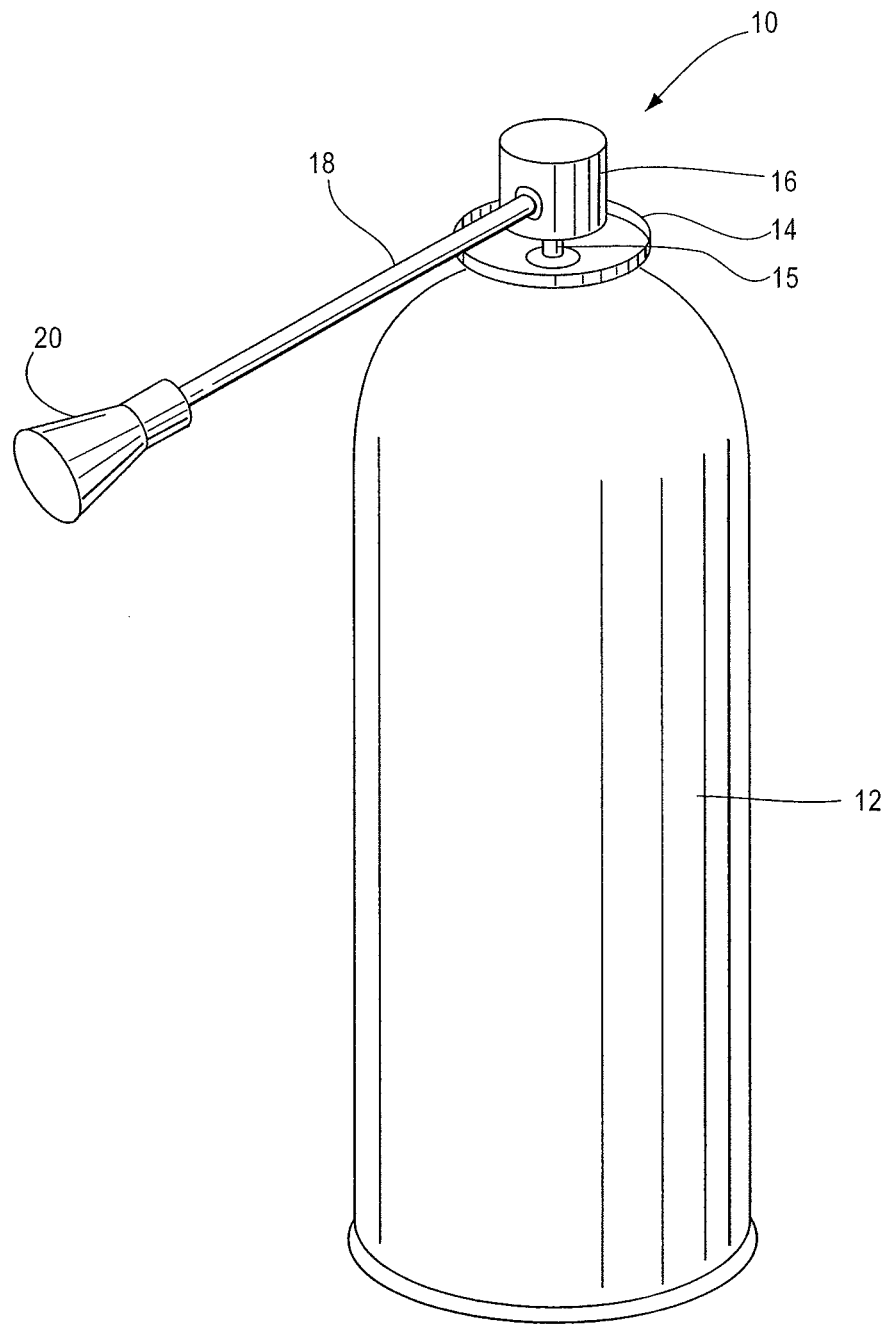
FIG. 1 illustrates a perspective view of a cryosurgical device in accordance with one embodiment of the present invention.

While this invention is susceptible of an embodiment in many different forms, there are shown in the drawings and will be described herein in detail specific embodiments thereof with the understanding that the present disclosure is to be considered as an exemplification of the principles of the invention. It is not intended to limit the specific illustrated embodiments.

Embodiments of the claimed invention include a cryosurgical device and system for cryosurgically treating skin lesions that provides for effective treatment of the abnormal tissue, that does not waste the coolant solution used in connection with the device, and that evenly distributes a controlled amount of coolant solution to a well defined area.

Figure 10:
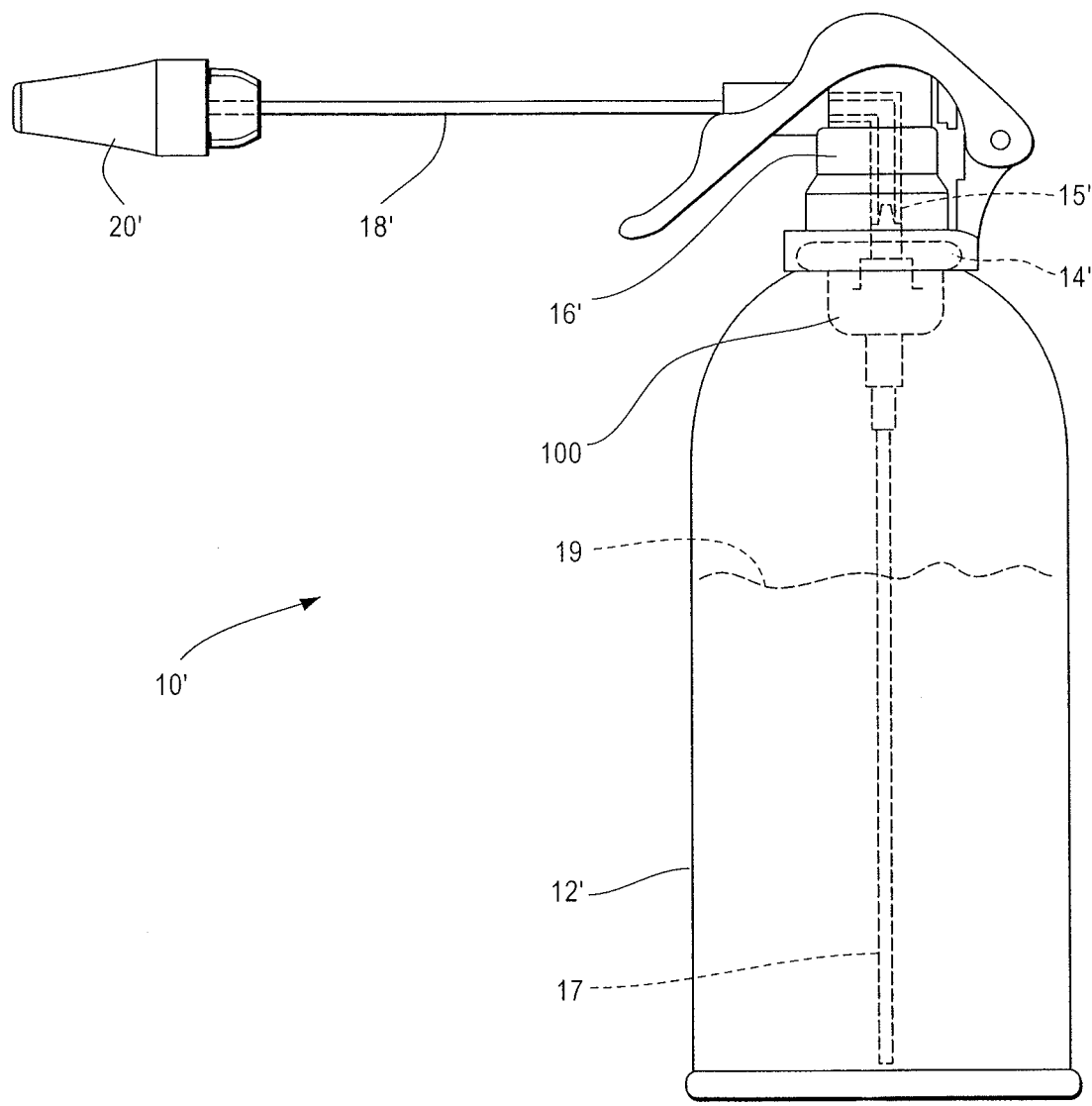
FIG. 10 illustrates a cross-sectional view of a cryosurgical device in accordance with a second embodiment of the present invention.

FIG. 1 illustrates a perspective view of a cryosurgical device 10 for use in a system in accordance with a first embodiment of the present invention. As seen in FIG. 10, the cryosurgical device 10 can incorporate a container 12. The container 12 can be made of, for example, steel or aluminum, and can be used to safely hold a coolant solution, for example, a liquid cryogen. In embodiments of the claimed invention, the container 12 can be pressurized and can be, for example, an aerosol container.

The container 12 can contain a coolant solution that can be used in connection with cryosurgically treating skin diseases, for example, skin lesions. The coolant solution can be, for example, liquid nitrogen, or any solution known by those of skill in the art to be used in cryosurgery. In embodiments of the claimed invention, the coolant solution can be a mixture of 95% dimethyl ether (DME) and 5% propane or a mixture of 95% DME, 2% propane, and 3% isobutene. In alternate embodiments, the coolant solution can be R-404a, which is a mixture of 52% 1,1,1-trifluoroethane, 44% pentafluoroethane, and 4% 1,1,1,2-tetrafluoroethane. It is preferred that the coolant solution has a boiling point below −20° F.

A system in accordance with the present invention comprises a cryosurgical device 10 that can incorporate a cup 14 housing a metered valve, as known by those of ordinary skill in the art, a valve stem 15, and an actuator 16. The cup 14 housing the metered valve 15 can seal the container 12, and the metered valve 15 can function in connection with the container 12 and the actuator 16. An extension tube 18 can extend from the actuator 16 away from the device 10, and an applicator head 20 can be located at a distal end of the extension tube 18.

In alternate embodiments of the claimed invention, a cryosurgical device can incorporate a cup housing a metered valve, an actuator, and an extension tube. A coolant solution can be dispersed from the container through the metered valve, the actuator, and extension tube. The coolant solution can exit a distal end of the extension tube and be applied to a treatment area with the use of, for example, a cone as is known by those of ordinary skill in the art.

Referring to FIG. 10, a cross-sectional view of a cryosurgical device in accordance with a second embodiment of the present invention is shown. Elements of the cryosurgical device 10' are most clearly illustrated in FIG. 10 and are described in further detail.

A metered valve assembly 100 can be incorporated into the device. The metered valve assembly 100 includes a valve cup 14', which seals the container and holds the metered valve. A dip tube 17 extends from the metered valve assembly 100 into the container 12' and directs the coolant solution 19 from the container 12' to the metered valve in the valve cup 14'.

When the actuator/trigger assembly 16' is at rest, a chamber in the metered valve fills up thereby measuring a predetermined amount of coolant solution 19. When the actuator/trigger assembly 16' is engaged, the coolant solution 19 is released from the chamber of the metered valve through the valve stem 15', through the actuator/trigger assembly 16', and into the applicator tube 18' thus delivering one dose of the predetermined amount of coolant solution 19 to the applicator head 20'. Different metered valves can measure different predetermined amounts of a coolant solution.

One actuation of the predetermined amount of coolant solution measured by the metered valve provides a single dose of the coolant solution. Accordingly, the metered valve to be used can be determined based upon the size of the abnormal tissue to be treated. That is, when a larger area is to be treated, a metered valve can be used that measures a larger predetermined amount of coolant solution. Similarly, when a smaller area is to be treated, a metered valve can be used that measures a smaller predetermined amount of coolant solution.

Alternatively, a metered valve that delivers a fixed volume of coolant solution can be used, and a practitioner can simply apply the coolant solution in multiple actuations as necessary to treat the treatment area. The delivery of the fixed amount of coolant solution can be repeated a defined number of times based on the size and area of the treatment area. For example, when the size and area of the treatment area are large enough to require more than the fixed amount of coolant solution delivered with one engagement of the actuator, the actuator can be engaged repeatedly until the desired amount of coolant solution has been delivered. A user will know the size and area of the treatment area prior to using the device. Accordingly, a user can calculate how much of the coolant solution is necessary to treat the treatment area. A user will also know the fixed amount of coolant solution that is delivered from the container with one engagement of the actuator. Accordingly, a user can calculate how many times he or she must engage the actuator to deliver the required amount of coolant solution for the particular treatment area being treated. In embodiments of the claimed invention, the metered valve can deliver from approximately 10 microliters with each engagement of the actuator up to a volume as large as would be known by those or ordinary skill in the art.

A practitioner observing an ice ball formed over the treatment area, can apply the coolant solution as necessary in multiple actuations as bubbling begins to dissipate. In this manner, the ice ball can be maintained for a longer period of time. A device 10' can be actuated one time or as many times as necessary. The freeze and thaw process of the ice ball can be repeated with further actuations of the device 10' as necessary.

Any type of actuator can be used to activate the metered valve assembly. FIG. 1 and FIG. 10 illustrate at least two types of actuators as are known by those of skill in the art. It is to be understood that the type of actuator employed is not a limitation of the present invention.

Each time the actuator is employed, one dose of coolant solution flows from the metered valve through the valve stem 15 or 15' to the extension tube 18 or applicator tube 18'. In embodiments of the claimed invention the applicator tube can be a flexible straw-like device of, for example, plastic or metal.

An applicator head 20 or 20' can be affixed to a distal end of the extension tube 18 or applicator tube 18'. The applicator head 20 or 20' receives the coolant solution from the tube 18 or 18' and pools the coolant solution over the abnormal tissue being treated.

Figure 2:
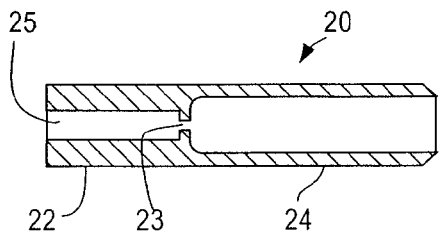
FIG. 2 illustrates a cross-sectional view of a first applicator head in accordance with a first embodiment of the present invention.

Referring to FIG. 2, a cross-sectional view of a first applicator head 20 in accordance with the first embodiment of the present invention is shown. The applicator head 20 can include three sections: a first section, 22, a second section 24, and a stop 23.

The first section 22 can include an extension tube slot 25, and a distal end of the extension tube 18 can be inserted therein. Accordingly, the extension tube slot 25 should have a diameter wide enough to allow the extension tube 18 to be inserted therein and small enough so that the extension tube 18 fits securely within the extension tube slot 25.

In embodiments of the system of the claimed invention, a practitioner can attach and remove an applicator head 20 relatively easily to the distal end of the extension tube 18. Further, a proximal end of the extension tube 18 can be removed and attached relatively easily to the actuator 16. In this manner, an applicator head and/or an extension tube can be discarded after use with one patient or one treatment area, and a new applicator head and/or extension tube can be attached when the device 10 is being used with a second patient or second treatment area. Alternatively, an applicator head and/or extension tube can be reusable by removing the applicator head from the extension tube and/or removing the extension tube from the actuator. The applicator head and/or extension tube can then be sterilized with, for example, autoclaving or a bactericidal solution, before reaffixing the applicator head to the extension tube and/or the extension tube to the actuator.

In alternate embodiments, an applicator head and the extension tube can be one continuous piece of material. In some embodiments of the claimed invention, the applicator head and the extension tube can be formed from separate pieces of material that are fused, welded, melted, snapped, clipped, pressure fit, or screwed together, for example, to form one continuous piece of material.

A stop 23 is located at the distal end of the first section 22. The stop 23 prevents the extension tube 18 from extending past the stop 23 in the applicator head 20.

A second section 24 is located at the distal end of the applicator head 20. As coolant solution exits the extension tube 18, the coolant solution can pass through the second section 24 and be delivered to the abnormal tissue to be treated. The distal end of the second section can be placed over or on the abnormal tissue being treated.

Figure 3:
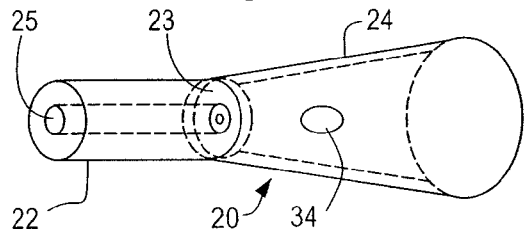
FIG. 3 illustrates a perspective view of a second applicator head in accordance with the first embodiment of the present invention.

FIG. 3 illustrates a perspective view of a second applicator head 20 in accordance with the first embodiment of the present invention. As seen in FIG. 3, the applicator head 20 includes a first section 22, which contains an extension tube slot 25 for receiving the distal end of the extension tube. The applicator head also includes a stop 23 for preventing the extension tube 18 from extending any further than the stop in the applicator head 20.

The second section 24 of the applicator head illustrated in FIG. 3 is conical in shape such that the distal end of the second section 24 is of a greater diameter than the proximal end of the second section 24. The larger distal end of the second section 24 can be used to treat abnormal tissue areas of larger sizes.

Figure 4A:
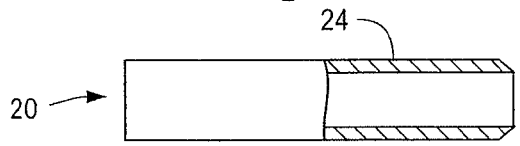
FIG. 4a illustrates a first cross-sectional view of an applicator head in accordance with the first embodiment of the present invention.
Figure 6A:
FIG. 6a illustrates a first end view of an applicator head in accordance with the present invention.
Figure 6B:
FIG. 6b illustrates a first bottom opening view of an applicator head in accordance with the present invention.
Figure 4B:
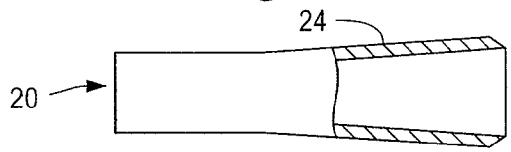
FIG. 4b illustrates a second cross-sectional view of an applicator head in accordance with the first embodiment of the present invention.
Figure 7A:
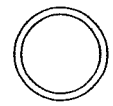
FIG. 7a illustrates a second end view of an applicator head in accordance with the present invention.
Figure 7B:
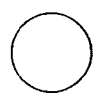
FIG. 7b illustrates a second bottom opening view of an applicator head in accordance with the present invention.
Figure 4C:
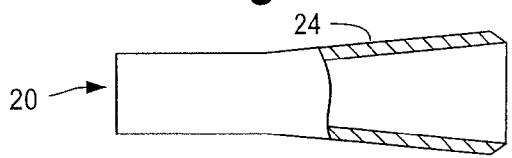
FIG. 4c illustrates a third cross-sectional view of an applicator head in accordance with the first embodiment of the present invention.
Figure 8A:
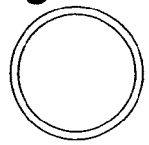
FIG. 8a illustrates a third end view of an applicator head in accordance with the present invention.
Figure 8B:
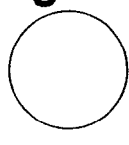
FIG. 8b illustrates a third bottom opening view of an applicator head in accordance with the present invention.

FIGS. 4a, 4b, 4c, and 4d illustrate first, second, third, and fourth cross-sectional views of an applicator head 20, respectively, in accordance with the first embodiment of the present invention. As can be seen in FIG. 4a, the second section 24 of the applicator head 20 can have a relatively uniform diameter throughout. Alternatively, as seen in FIGS. 4b, 4c, and 4d, the second section 24 can be a conical shape and increase in diameter towards the distal end of the applicator head to varying degrees.

The treatment area to be treated with the device 10 can be of varying size and area. Accordingly, applicator heads with varying diameters of the distal ends of the second sections can be used in connection with the device 10. The diameter of the distal end of the second section 24 determines the size and area that the coolant solution emitted from the applicator head 20 will reach. For example, when the treatment area is small, an applicator head with a second section having a uniform diameter, as seen in FIG. 4a can be used. As the size of the treatment area increases, an actuator head with a second section having larger diameters at the distal end can be used, for example, the applicator heads as seen in FIGS. 4b and 4c.

FIGS. 6a, 6b, 7a, 7b, 8a, 8b, 9a, and 9b illustrate alternative end views and bottom opening views of an applicator head in accordance with the present invention. As seen in FIGS. 6a, 6b, 7a, 7b, 8a, 8b, 9a, and 9b, the end views and bottom opening views can have varying diameters in alternative embodiments of the present invention. The diameters could be, for example, 0.125 inches, 0.25 inches, 0.375 inches, or 0.5 inches.

As explained above, the size of the diameter to be used in connection with a particular treatment can be determined based on the size of the treatment area. For example, when the treatment area is small, a small diameter can be used. When the treatment area is larger, a larger diameter can be used. In this manner, the size of the applicator head allows for targeted application of the coolant solution to the treatment area. The coolant solution is applied to a precisely demarcated area defined by the size of the distal end of the second section of the applicator heard. Accordingly, coolant solution is not wasted, but coolant solution is still effectively administered to the treatment area.

Figure 5:
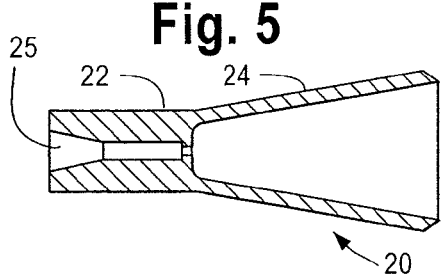
FIG. 5 illustrates a fourth cross sectional view of an applicator head in accordance with the first embodiment of the present invention.
Figure 9A:
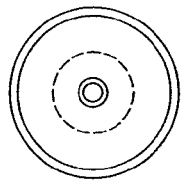
FIG. 9a illustrates a fourth end view of an applicator head in accordance with the present invention.
Figure 9B:
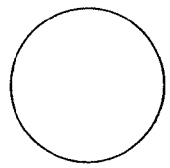
FIG. 9b illustrates a fourth bottom opening view of an applicator head in accordance with the present invention.

FIG. 5 illustrates a fourth cross sectional view of an applicator head in accordance with the first embodiment of the present invention. As seen in FIG. 5, the applicator head 20 can be, for example, 1 inch in length. The first section 22 of the applicator head 20 can be, for example, 0.5 inches in length and 0.25 inches in width. The wall of the second section 24 can be, for example, 0.0625 inches thick. It is to be understood that the exact dimensions of the applicator head are not limitations of the present invention.

The second section 24 of the applicator head 20 can include at least one vent hole 34, as seen in FIG. 3. In embodiments of the claimed invention, the second section 24 can include, for example, four vent holes.

The vent holes allow air from the atmosphere to reach the treatment area. When ambient air reaches the coolant solution applied to the treatment area, an ice ball can form, and the evaporation, bubbling, and thawing processes can occur.

Figure 11:
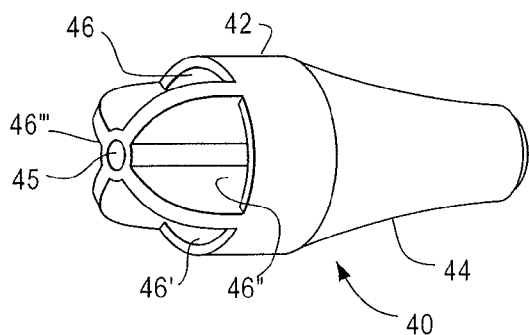
FIG. 11 illustrates a perspective view of an applicator head in accordance with a second embodiment of the present invention.

Referring now to FIG. 11, a perspective view of an applicator head in accordance with a second embodiment of the present invention is shown. As seen in FIG. 11, the applicator head 40 includes a first section 42 and a second section 44. The second section 44 is situated at the distal end of the applicator head 40, and the distal end of the second section 44 can be placed over a treatment area.

The distal end of the second section 44 can have different diameters. For example, the distal end of the second section 44 can be large enough so that the diameters of the proximal and distal ends of the second section are relatively equal, and the second section has a relatively uniform diameter throughout. Alternatively, the diameter of the distal end of the second section can be smaller than the diameter of the proximal end of the second section. The distal end of the second section can be, for example, 3 mm, 5 mm, 7 mm, 9 mm, or 12 mm.

The first section 42 of the applicator head 40 can include an extension tube slot 45 such that an applicator tube can be placed therein. The first section can also include, for example, four vent openings 46, 46', 46", and 46'". The vent openings can be directed towards the proximal end of the applicator tube. Further, the vent openings can allow ambient atmosphere to reach the treatment area and dispersed coolant solution so that an ice ball can form, and the evaporation, bubbling, and thawing processes can occur.

Figure 12:
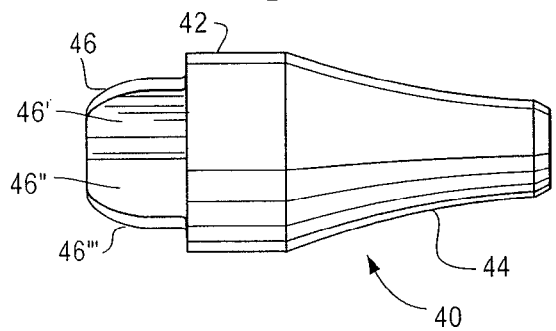
FIG. 12 illustrates a side view of an applicator head in accordance with the second embodiment of the present invention.
Figure 13:
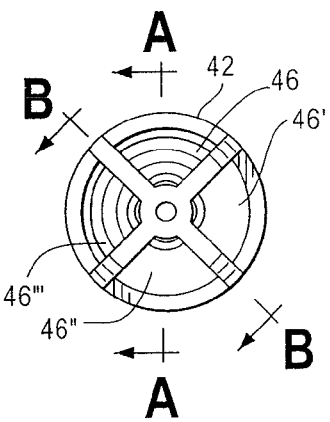
FIG. 13 illustrates an end view of an applicator head in accordance with the second embodiment of the present invention.
Figure 13A:
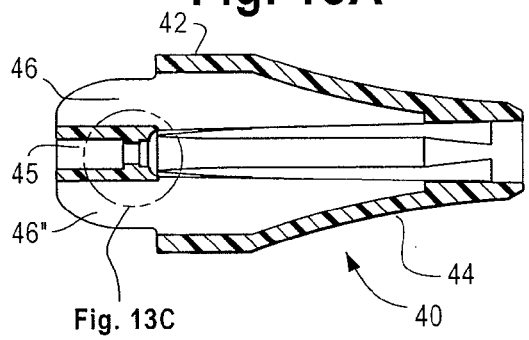
FIG. 13a illustrates a cross-sectional view of line A-A of an applicator head in accordance with the second embodiment of the present invention.
Figure 13B:
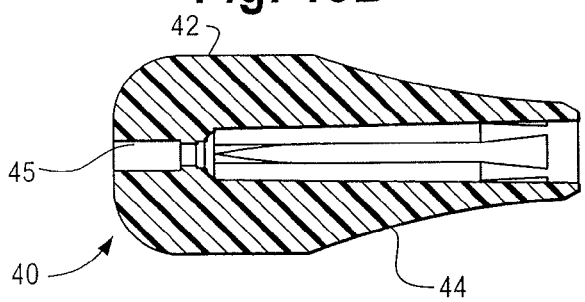
FIG. 13b illustrates a cross-sectional view of line B-B of an applicator head in accordance with the second embodiment of the present invention.

FIG. 12 illustrates a side view of the applicator head illustrated in FIG. 11. As seen in FIG. 12, the vent openings 46, 46', 46", and 46'" can be situated at the proximal end of the first section 42. The distal end of the second section 44 can have different diameters suitable for treating skin lesions of varying size. For example, when the treatment area is small, an applicator head with a second section having a distal end with a small diameter can be used. As the size of the treatment area increases, an applicator head with a second section having larger diameters at the distal end can be used. For example, an applicator head with a distal end of the second section having a diameter as large as the diameter of the proximal end of the second section can be used such that the second section has a relatively uniform diameter throughout FIG. 13 illustrates an end view of the proximal end of the first section of the applicator head illustrated in FIGS. 11 and 12. As seen in FIG. 13, the vent openings 46, 46', 46", and 46'" can be defined by pieces of the first section 42 forming an "X". FIG. 13a illustrates a cross-sectional view of the line A-A in FIG. 13, and FIG. 13b illustrates a cross-sectional view of the line B-B in FIG. 13.

Figure 13C:
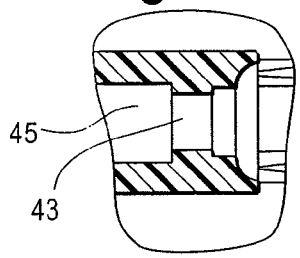
FIG. 13c illustrates a detailed view of a stop located in an applicator head in accordance with the second embodiment of the present invention.

As seen in FIG. 13a, the vent openings 46 and 46" extend from the first section 42 through the second section 44 and are situated about the applicator tube slot 45. Referring to FIG. 13c, a detailed view of a stop located in an applicator head is shown. The stop 43 is located at the distal end of the applicator tube slot 45 to prevent the applicator tube from extending past the stop 43 in the applicator head 40.

The applicator head in accordance with the second embodiment of the present invention as shown in FIG. 11 through FIG. 13c can be, for example, 1.4 inches in length and 0.6 inches in width at its widest point. It is to be understood that the exact dimensions of the applicator head are not limitations of the present invention.

While the applicator heads depicted in FIGS. 2-9b and FIGS. 11-13c have been described above with reference to various sections, it is to be understood that an applicator head in accordance with the present invention is one continuous piece of material. The reference to various sections is merely for clarity in describing the applicator head as a whole. In embodiments of the claimed invention, the applicator head can be formed from separate pieces of material that are fused, welded, melted, snapped, clipped, pressure fit, or screwed together, for example, to form one continuous piece of material.

It is to be further understood that the applicator heads depicted in FIGS. 2-9b and FIGS. 11-13c are merely exemplary in size and shape. While the distal end of the applicator head as illustrated is round, the shape of the distal end of the applicator head can be round, oval, square, or any other shape as would be understood by those or ordinary skill in the art.

Applicator heads in accordance with the present invention can be made of, for example, plastic or metal. In embodiments of the claimed invention, the applicator head can be made of a clear material. In this manner, a practitioner can more effectively view and assess the treatment area, ensure that the applicator head is precisely placed over the treatment area, and see that an ice ball has been formed and maintained for a sufficient period of time.

From the foregoing, it will be observed that numerous variations and modifications may be effected without departing from the spirit and scope of the invention. It is to be understood that no limitation with respect to the specific apparatus or method illustrated herein is intended or should be inferred. It is, of course, intended to cover by the appended claims all such modifications as fall within the scope of the claims.

What is claimed:

1. A cryosurgical system for the application of a coolant solution onto a skin surface of a patient comprising: a pressure container; a metered valve that manually regulates retrieval of the coolant solution stored in the pressurized container and is configured to emit a measured volume of coolant solution onto the skin surface of the patient with each actuation of the system; an actuator that engages the metered valve when engaged and directs the measured volume of coolant solution to an extension tube, the extension tube being configured to direct the coolant solution away from the pressurized container and onto the skin surface of the patient; said metered valve allowing consecutive multiple engagements in succession by the actuator for the emission of multiple measured volumes of coolant solution; an applicator head having a first section with a proximal observation portion and a second section with a distal treatment portion, the applicator head being positioned to receive coolant solution delivered through the extension tube; the distal treatment portion of the applicator head comprising an open-ended enclosure that is configured to confine the coolant solution to a precisely demarcated skin surface area of the patient, wherein the second section of the applicator head comprises a passageway disposed between the extension tube and the enclosure through which coolant passes; and the proximal observation portion of the applicator head having at least one vent opening that extends from the first section through the second section, said vent opening being configured to be open to ambient atmosphere and to the patient skin surface when the distal treatment portion is in contact therewith, whereby coolant solution evaporation proceeds to ice ball formation, and said vent opening is configured to enable observation of the ice ball by the user of the system, whereby the user determines if the metered valve is to actuate another measured volume of coolant solution to the applicator head distal treatment portion.

2. The cryosurgical system of claim 1 wherein the pressurized container is an aerosol container.

3. The cryosurgical system of claim 1 wherein the metered valve is located in a cup situated atop the pressurized container.

4. The cryosurgical system of claim 1 wherein the extension tube is one of plastic or metal.

5. The cryosurgical system of claim 1 wherein the extension tube is attached to the applicator head which includes an extension tube slot for receiving the extension tube therein.

6. The cryosurgical system of claim 1 wherein the applicator head is one of plastic or metal.

7. The cryosurgical system of claim 1, wherein the applicator head first section receives the extension tube, the second section is distally located from the extension tube, and a stop is located at a distal end of the first section to prevent the extension tube from entering the second section.

8. The cryosurgical system of claim 7 wherein the first section contains a hollow tube for receiving the extension tube.

9. The cryosurgical system of claim 7 wherein the second section has a uniform diameter throughout.

10. The cryosurgical system of claim 7 wherein a diameter of a distal end the second section is smaller than a diameter of a proximal end of the second section.

11. The cryosurgical system of claim 7 wherein a diameter of a distal end of the second section is larger than a diameter of a proximal end of the second section.

12. The cryosurgical system of claim 1 wherein the applicator head is formed from clear plastic.

13. The cryosurgical system of claim 1 wherein the applicator head has a plurality of vent openings located therein.

14. A cryosurgical system for the application of a coolant solution onto a skin surface of a patient comprising: a pressurized container; a metered valve that manually regulates a retrieval of a certain amount of the coolant solution stored in the pressurized container and regulates said certain amount of the coolant solution with each actuation of the system; an actuator that engages the metered valve and when engaged directs the certain amount of the coolant solution to an extension tube wherein the extension tube directs the certain amount of the coolant solution away from the pressurized container toward a distal end of the extension tube for dispensing the coolant solution out of the extension tube and onto abnormal tissue of a patient; an applicator head having a first section with a proximal observation portion and a second section with a distal treatment portion, the applicator head being positioned to receive coolant solution delivered through the extension tube; the distal treatment portion of the applicator head comprising an open-ended enclosure that is configured to confine the coolant solution to a precisely demarcated skin surface area of the patient, wherein the second section of the applicator head comprises a passageway disposed between the extension tube and the enclosure through which coolant passes; and the proximal observation portion of the applicator head having at least one vent opening that extends from the first section through the second section, said vent opening being configured to be open to ambient atmosphere and to the patient skin surface when the distal treatment portion is in contact therewith, whereby coolant solution evaporation proceeds to ice ball formation, and said vent opening is configured to enable observation of the ice ball by the user of the system, whereby the user determines if the metered valve is to actuate another measured volume of coolant solution to the applicator head distal treatment portion.

15. A cryosurgical device for the application of a coolant solution onto a skin surface of a patient comprising: a metered valve that manually regulates retrieval of the coolant solution stored in a pressurized container and is configured to emit a measured volume of coolant solution onto the skin surface of the patient with each actuation of the system; an actuator that engages the metered valve when engaged and directs the measured volume of coolant solution to an extension tube, the extension tube being configured to direct the coolant solution onto the skin surface of the patient; said metered valve allowing consecutive multiple engagements in succession by the actuator for the emission of multiple measured volumes of coolant solution; an applicator head attached to a distal end portion of the extension tube, the applicator head having a first section with a proximal observation portion and a second section with a distal treatment portion; the distal treatment portion of the applicator head comprising an open-ended enclosure that is configured to confine the coolant solution to a precisely demarcated skin surface area of the patient, wherein the second section of the applicator head comprises a passageway disposed between the extension tube and the enclosure through which coolant passes; and the proximal observation portion of the applicator head having at least one vent opening that extends from the first section through the second section, said vent opening being configured to be open to ambient atmosphere and to the patient skin surface when the distal treatment portion is in contact therewith, whereby coolant solution evaporation proceeds to ice ball formation, and said vent opening is configured to enable observation of the ice ball by the user of the system, whereby the user determines if the metered valve is to actuate another measured volume of coolant solution to the applicator head distal treatment portion.

16. A cryosurgical device for the application of a coolant solution onto a skin surface of a patient comprising: a metered valve that manually regulates retrieval of the coolant solution stored in a pressurized container and is configured to emit a measured volume of coolant solution onto the skin surface of the patient with each actuation of the system; an actuator that engages the metered valve when engaged and directs the measured volume of coolant solution to an extension tube, the extension tube being configured to direct the coolant solution onto the skin surface of the patient; said metered valve allowing consecutive multiple engagements in succession by the actuator for the emission of multiple measured volumes of coolant solution; an applicator head having a first section with a proximal observation portion and a second section with a distal treatment portion, the applicator head being positioned to receive coolant solution delivered through the extension tube; the distal treatment portion of the applicator head comprising an open-ended enclosure that is configured to confine the coolant solution to a precisely demarcated skin surface area of the patient, wherein the second section of the applicator head comprises a passageway disposed between the extension tube and the enclosure through which coolant passes; and the proximal observation portion of the applicator head having at least one vent opening that extends from the first section through the second section, said vent opening being configured to be open to ambient atmosphere and to the patient skin surface when the distal treatment portion is in contact therewith, whereby coolant solution evaporation proceeds to ice ball formation, and said vent opening is configured to enable observation of the ice ball by the user of the system, whereby the user determines if the metered valve is to actuate another measured volume of coolant solution to the applicator head distal treatment portion.

* * * * *